US009675638B2

(12) United States Patent
Canals Almazán et al.

(10) Patent No.: US 9,675,638 B2
(45) Date of Patent: Jun. 13, 2017

(54) USE OF TUNGSTEN (VI) SALTS FOR THE TREATMENT OF FEMALE INFERTILITY IN NON-DIABETIC MAMMALS

(71) Applicant: OXOLIFE, S.L., Sant Quirze de Vallès (ES)

(72) Inventors: Ignacio Canals Almazán, Sant Quirze de Vallès (ES); Agnès Arbat Bugié, Barcelona (ES)

(73) Assignee: OXOLIFE, S.L., Sant Quirze del Vallés (ES)

( * ) Notice: Subject to any disclaimer, the term of this patent is extended or adjusted under 35 U.S.C. 154(b) by 0 days.

(21) Appl. No.: 14/762,603

(22) PCT Filed: Jan. 21, 2014

(86) PCT No.: PCT/EP2014/051141
§ 371 (c)(1),
(2) Date: Jul. 22, 2015

(87) PCT Pub. No.: WO2014/114644
PCT Pub. Date: Jul. 31, 2014

(65) Prior Publication Data
US 2015/0359820 A1 Dec. 17, 2015

(30) Foreign Application Priority Data
Jan. 22, 2013 (ES) .................. 201330071

(51) Int. Cl.
*A61K 33/24* (2006.01)

(52) U.S. Cl.
CPC .................. *A61K 33/24* (2013.01)

(58) Field of Classification Search
CPC .................. A61K 33/24
USPC .................. 424/617
See application file for complete search history.

(56) References Cited

U.S. PATENT DOCUMENTS

| | | | |
|---|---|---|---|
| 4,328,134 A * | 5/1982 | Schally | C07K 5/0825 525/54.11 |
| 7,122,209 B2 * | 10/2006 | Gomis De Barbara | A61K 33/24 424/617 |
| 2006/0100154 A1 * | 5/2006 | Koch | A61K 38/09 514/9.9 |
| 2008/0206356 A1 | 8/2008 | Guinovart Cirera et al. | |

FOREIGN PATENT DOCUMENTS

| | | |
|---|---|---|
| ES | 2108642 A1 | 12/1997 |
| ES | 2275873 T3 | 6/2007 |

OTHER PUBLICATIONS

Agarwal et al. "Oxidative stress and its implications in female infertility—a clinician's perspective" a Review article in Reproductive BioMedicne, vol. 11 m Issue 2, 2005, pp. 641-650).*
Burks et al. ("IRS-2 pathways integrate female reproduction and energy homeostasis" in Nature, vol. 407, No. 6802, pp. 377-382, 2000.*
Vause et al. ("Ovulation Induction in Polycystic Ovary Syndrome" in SOGC Clinical Practice Guideline, No. 242, May 2010.*
Ballester, J. et al., "Tungstate administration improves the sexual and reproductive function in female rats with streptozotocin-induced diabetes," *Human Reproduction*, vol. 22, No. 8, pp. 2128-2135, 2007.
Burks, D. J. et al., "IRS-2 pathways integrate female reproduction and energy homeostasis," *Nature*, vol. 407, No. 6802, pp. 377-382, 2000.
Gonzáles Sanz, S.M. et al., "Genetic manipulation of IRS proteins: animal models for understanding the molecular basis of diabetes," *Avances En Diabetología*, vol. 25, pp. 21-26, 2009.
Sharma, S. et al., "Female infertility: an overview," *International Journal of Pharmaceutical Sciences and Research*, vol. 2, No. 1, pp. 1-12, 2011.
International Search Report for PCT/EP2014/051141, mailed on May 5, 2014.
Nithers et al. "Disruption of IRS-2 causes type 2 diabetes in mice" Nat. 1998, vol. 391, pp. 900-904.
Kubota et al. "Disruption of Insulin Receptor Substrate 2 Causes Type 2 Diabetes Because of Liver Insulin Resistance and Lack of Compensatory ?-Cell Hyperplasia" Diabetes 2000, vol. 49, pp. 1880-1889.
Xiuna Jin, Effect of obesity on reproductive function and improvement of weight loss on reproductive function of woman with obesity but no. ovulation. Medicine Health Sciences of Chinese Master's Theses, Full-text Database, E065-103. ,7.

* cited by examiner

*Primary Examiner* — Blessing M Fubara
(74) *Attorney, Agent, or Firm* — McCarter & English, LLP; Danielle L. Herritt

(57) ABSTRACT

The present invention comprises the use of a therapeutically effective amount of a tungsten (VI) salt with a pharmaceutically or veterinarily acceptable cationic group, or a solvate of said salt, for the preparation of a medicinal product for the treatment of female infertility in non-diabetic mammals.

15 Claims, No Drawings

USE OF TUNGSTEN (VI) SALTS FOR THE TREATMENT OF FEMALE INFERTILITY IN NON-DIABETIC MAMMALS

RELATED APPLICATIONS

This application is a 35 U.S.C. §371 national stage filing of International Application No. PCT/EP2014/051141, filed on Jan. 21, 2014, which claims priority to Spanish Patent Application No. P 201330071, filed on Jan. 22, 2013. The entire contents of each of the foregoing applications are incorporated herein by reference.

The invention relates to the field of fertility. Particularly, it relates to the use of tungsten (VI) salts for the treatment of female infertility.

STATE OF THE ART

Infertility can be defined as the inability to achieve pregnancy in a period of 1 year of regular unprotected sexual intercourse. Particularly, female infertility can refer to the inability to conceive and/or to carry a pregnancy to term. Despite the difficulties in estimating the prevalence of infertility, it is generally accepted that one out of every four women is infertile at a certain stage of the reproductive age.

The main causes of infertility among women include ovulatory dysfunctions, reproductive tract pathologies, reduced oocyte quality and follicular depletion inherent to aging. However, there are also a considerable percentage of women with unexplained infertility, also called idiopathic infertility, one of the possible causes of which could be related to deficiencies in the implantation process.

Particularly, among the many biological causes of infertility in women, causes relating to disorders in hormonal stimuli which regulate follicular development, ovulation, migration of the immature ovule (oocyte), as well as subsequent conception and zygote implantation in the uterine wall, can be highlighted. This entire process is regulated by hormonal secretions of specific endocrine organs, such as the hypophysis, the hypothalamus and the thyroid gland, for example.

Therefore, ovulation disorders such as the lack of ovulation, as well as pathologies associated with anatomical and functional disorders of the reproductive tract and of the uterus that can alter zygote implantation can be highlighted among the main causes of infertility.

Different treatments for female infertility are known, including the administration of medicinal products for treating infertility related to hormonal problems such as ovulation disorders, as well as in vitro fertilization and intrauterine insemination techniques.

However, the percentage of pregnancies achieved by means of the above mentioned treatments has some limitations. Thus, for example, it has been observed that the treatment of women whose ovulation is irregular or absent by means of administering clomiphene citrate, a drug of the stilbene family, allows restoring ovulation in a high percentage, but the pregnancy rate remains being low, about equal to or less than 50%.

On the other hand, in vitro fertilization treatments are very effective in the oocyte fertilization stage. However, the transfer rate (implantation of embryos in the uterine wall) is low. This leads to multiple embryo transfers for each in vitro fertilization cycle, with the consequence of a higher percentage of high-risk multiple pregnancies.

Finally, it is known that metabolic disorders such as diabetes or obesity entail a limitation of fertility. It is known that partial or complete recovery of glycemia, insulinemia and/or body weight in obese or diabetic female mice with damaged reproductive function involves an improvement in fertility.

Different pharmacological treatments, such as metformin or tungsten (VI) salts, or even lifestyle changes, have been demonstrated to improve diabetes or insulin disorders, such as insulin deficiency or insulin resistance for example, achieving a completely or partially recovering of the reproductive function. In the specific case of sodium tungstate, it is known that rats with streptozotocin injection-induced insulinopenia and diabetes partially recover circulating insulin levels after a prolonged treatment (10 weeks) with sodium tungstate as a result of partially reversing diabetes. Subsequently, when the aforementioned female rats partially recovered from diabetes mate with healthy male rats, it is observed that, parallel to the partial recovery from diabetes, the female rats have partially recovered their reproductive capacity. Particularly, it is observed that the percentage of births with respect to the number of positive curettages in female mice which had partially recovered from diabetes after treatment with sodium tungstate increases up to 66%, this percentage being lower than the female mice that did not have diabetes where the percentage is 100% (cf. J. Ballester et. al., "Tungstate administration improves the sexual and reproductive function in female rats with streptozotocin-induced diabetes", *Human Reproduction*, 2007, vol. 22, pp. 2128-2135).

In summary, despite progress in treatments of female infertility, there are still patients who cannot benefit from the therapies available today due to their ineffectiveness. Therefore, there is still a need to find new therapies for treating female infertility to give greater efficiency.

DESCRIPTION OF THE INVENTION

The inventors have discovered that the use of a therapeutically effective amount of a tungsten (VI) salt with a pharmaceutically or veterinarily acceptable cationic group, or a solvate of said salt, is useful for the preparation of a medicinal product for the treatment of infertility in non-diabetic female mammals.

Even though it is known that sodium tungstate can partially reverse reproductive function disorders in diabetic female mice since it normalizes blood glucose levels, the state of the art neither describes nor suggests that sodium tungstate can have activity by itself on the function of the female reproductive system for the treatment of female infertility.

It must be pointed out in the state of the art that sodium tungstate has demonstrated to be effective in normalizing glucose levels. Particularly, document EP1400246 discloses a pharmaceutical composition of a tungsten (VI) compound for reducing blood glycemia in humans with type 1 diabetes (IDDM) or type 2 diabetes (NIDDM).

The inventors of the present invention have demonstrated that tungsten (VI) salts are an effective treatment for recovering ovulation and/or increasing oocyte implantation regardless of the changes in glucose metabolism or the changes in body weight, and accordingly, the administration of a tungsten (VI) salt is effective for the treatment of infertility in non-diabetic female mammals.

This aspect can also be formulated as a therapeutically effective amount of a tungsten (VI) salt with a pharmaceutically or veterinarily acceptable cationic group, or a solvate of said salt, for use in the treatment of infertility in non-diabetic female mammals. It also relates to a method for the treatment of a disease or condition occurring with infertility in non-diabetic female mammals which comprises administering a therapeutically effective amount of a tungsten (VI) salt with a pharmaceutically or veterinarily acceptable cationic group, or a solvate of said salt of the present invention, to mammals in need of said treatment.

The preferred and particular embodiments described below relate to the use of a therapeutically effective amount of a tungsten (VI) salt with a pharmaceutically or veterinarily acceptable cationic group, or a solvate of said salt, for the preparation of a medicinal product for the treatment of infertility in non-diabetic female mammals are also preferred and particular embodiments of a tungsten (VI) salt with a pharmaceutically or veterinarily acceptable cationic group, or a solvate of said salt, for use in the treatment of infertility in non-diabetic female mammals, as well as of a method for the treatment of a disease or condition occurring with infertility in non-diabetic female mammals. Furthermore, the present invention encompasses all the possible combinations of preferred and particular embodiments described herein.

As used herein, the expression "pharmaceutically or veterinarily acceptable cationic group" refers to any non-toxic inorganic or organic acceptable cation, capable of forming therapeutically effective tungsten (VI) salt and being suitable for use in veterinary or pharmaceutical therapy.

The tungstate anion is always accompanied by a cationic group forming a neutral tungstate salt. In one embodiment of the present invention, the tungsten (VI) salts are those salts comprising cationic groups selected from the group consisting of alkaline earth or alkaline cations. The salts whose cationic group of which is selected from the group consisting of sodium, potassium, magnesium and calcium are preferred. Preferably, the tungsten (VI) salt is the sodium salt of tungsten (VI).

The solvates of the tungsten (VI) salts and the use thereof for the preparation of a medicinal product for the treatment of female infertility in non-diabetic mammals are also part of the invention. In one embodiment of the invention, the solvate is the dihydrate solvate of a tungsten (VI) salt as defined above. Preferably, the solvate of the tungsten (VI) salt is the sodium tungstate dihydrate which is commercially available.

In one embodiment of the invention, the mammal is a human. In a preferred embodiment, the tungsten (VI) salt of the present invention is useful for the preparation of a medicinal product for the treatment of female infertility occurring with a change in the hypothalamic-pituitary axis. The diseases or conditions occurring with a change in the hypothalamic-pituitary axis include, among others, polycystic ovarian syndrome, metabolic syndrome, hyperprolactinemia, endometriosis, eating disorders, obesity, hypothyroidism, multiple sclerosis, rheumatoid arthritis, lupus erythematosus, cirrhosis, celiac disease, chronic renal failure and idiopathic causes.

In a preferred embodiment, the tungsten (VI) salt of the present invention is useful for the preparation of a medicinal product for the treatment of female idiopathic infertility. The concepts "idiopathic infertility" or "infertility without an apparent cause" or "unexplained infertility" have the same meaning and are used interchangeably. These concepts refer to those infertility cases in which the reason for the inability to achieve pregnancy has not been found in the standard sterility tests.

In another preferred embodiment, the tungsten (VI) salt of the present invention is useful for the preparation of a medicinal product for the treatment of female infertility due to eating disorders. The eating disorders occurring with a change in the hypothalamic-pituitary axis include, among others, anorexia nervosa and bulimia.

The term "ovulation" is understood as that process through which a woman releases oocytes into the uterus, and the term "restoring ovulation" is understood as the process through which the menstrual cycle is re-established, i.e., it is re-established the process of regularly releasing the oocyte into the uterus in women that did not ovulate (anovulation) or ovulated irregularly (oligoovulation). It means that the tungsten (VI) salt of the present invention is useful for the preparation of a medicinal product for the treatment of female infertility of women with incapacity of ovulation (anovulation) or women with the necessity of improving the efficiency of ovulation (oligoovulation).

As clearly shown in the results of Table 1 in the examples, the administration of a tungsten (VI) salt allows rapidly restoring the estrous cycle (after only 7 days since the start of treatment) in 100% of the treated non-diabetic female mice. Ovulation is restored within a time period in which the administration of the tungsten (VI) salt of the present invention does not modify body weight or glycemia of the treated female mice (cf. Tables 3 and 4). Therefore, one embodiment of the invention relates to the use of the tungsten (VI) salt defined above, or a solvate thereof, for the preparation of a medicinal product for the treatment of female infertility which comprises restoring ovulation.

On the other hand, as clearly shown in the results of Table 2 in the examples, the administration of a tungsten (VI) salt allows implantation of an average of 5 implanted embryos or young born in 80% of the treated non-diabetic female mice that restored their normal estrous cycle. Therefore, one embodiment of the invention relates to the use of a tungsten (VI) salt defined above, or a solvate thereof, for the preparation of a medicinal product for the treatment of female infertility which comprises increasing zygote implantation in the uterine wall.

The term "increasing zygote implantation" is understood as the process through which the efficiency of the implantation of the oocytes into the uterus is increased. It means that the tungsten (VI) salt of the present invention is useful either for increasing the number of oocytes implanted into the uterus or for improving the chance of successful pregnancy without increasing the risk of multiple pregnancies.

One embodiment of the invention relates to the use of the tungsten (VI) salt defined above, or a solvate thereof, for the preparation of a medicinal product for the treatment of female infertility which comprises restoring ovulation and increasing zygote implantation in the uterine wall.

Therefore, the use of a tungsten (VI) salt is useful for the treatment of female infertility by increasing the pregnancy rate. The treatment of the present invention can be useful as an alternative pharmacological treatment with respect to those already existing treatments for normalizing ovulation and/or increasing oocyte implantation in the uterine wall, or as treatment associated with intrauterine insemination and/or in vitro fertilization techniques to increase the embryo implantation rate in the transfer phase.

One embodiment of the invention relates to the use of the tungsten (VI) salt, or a solvate thereof when said tungstate salt is part of a pharmaceutical or veterinary composition further comprising pharmaceutically or veterinarily acceptable excipients or carriers. In one embodiment of the invention, the pharmaceutical or veterinary composition is a composition for oral administration. Solid oral compositions such as tablets and capsules, and liquid oral compositions such as oral solutions or suspensions, are of special interest.

The expression "pharmaceutically or veterinarily acceptable excipient or carrier" refers to the excipients or carriers suitable for use in pharmaceutical or veterinary technology for the preparation of the compositions for medical use. These components, excipients and carriers, must be compatible with the other ingredients of the composition. It must also be suitable for use in contact with human or animal tissues or organs without excessive toxicity, irritation, allergic response, or other immunogenicity problems or complications with a reasonable risk/benefit ratio.

Tungsten (VI) salts have been used in therapy for the treatment of obesity or diabetes. As used herein, the expression "therapeutically effective amount" refers to the amount of the tungsten (VI) salt which, when administered, is sufficient for the treatment of female infertility defined in the present invention. The specific doses of the tungsten (VI) salt according to this invention is determined by the particular circumstances surrounding the case, including, for example, the administered salt, the administration route, the administered pharmaceutical or veterinary composition, as well as the characteristics of the patient including, among others, height, weight and age; and the nature and stage of the disease. For example, an amount of a tungsten (VI) salt defined above comprised from 50 to 500 mg/kg/day can be used.

Generally in rodents the therapeutically effective amount of the tungsten (VI) salt for the treatment of female infertility as defined above can be comprised from 100 to 350 mg/kg/day. Preferably, the pharmaceutically effective amount is comprised from 150 to 280 mg/kg/day.

The effect of the tungsten (VI) salt for the treatment of female infertility in non-diabetic mammals in an animal model named IRS−/− has been demonstrated in the examples of the present invention. These female mice are a good non-diabetic infertile mouse model. Furthermore, this animal model is also a good model for non-diabetic infertile women.

Throughout the description and claims the word "comprises" and its variants do not intend to exclude other technical features, additives, components or steps. Furthermore, the word "comprises" includes "consists of". For persons skilled in the art, other objects, advantages and features of the invention will be understood in part from the description and in part from the practice of the invention. The following examples are provided by way of illustration and do not intend to limit the present invention.

EXAMPLES

1. Description of the Animal Model (IRS2−/− Female Mice)

The $IRS2^{-/-}$ mouse model is an Irs2 gene knock-out mouse model (Burks et. al., "IRS-2 pathways integrate female reproduction and energy homeostasis", *Nature,* 2000, vol. 407, pp. 377-382). Irs2 gene deletion translates into a clear sexual dimorphism in relation to fertility and carbohydrate metabolism.

The male mice of this model present insulin resistance and severe hyperglycemia that started at an early age. In contrast, the female mice remain relatively euglycemic up until later ages (4-5 months).

$IRS2^{-/-}$ female mice show low follicular development and persistent anovulation, accompanied by the absence of the estrous cycle in most of the mice.

The pregnancy rate in $IRS2^{-/-}$ female mice is 9% compared to a rate of 100% in $IRS^{wt}$ ($IRS\text{-}2^{+/+}$ wild type) female mice.

2. Ovulation, Implantation and Pregnancy Study

A. Animals

10 $IRS2^{-/-}$ female mice of ages comprised between 6 and 8 weeks. 6 "wild-type" ($IRS2^{wt}$) male mice of ages comprised between 6 and 8 weeks.

The female and male mice were housed separately in normal conditions, i.e., 12-hour light/darkness cycle and controlled moisture and temperature. The animals were voluntarily fed (also named ad libitum) with a standard feed diet.

B. Method

Pre-Treatment Phase

After a period of acclimation, the $IRS2^{-/-}$ female mice were housed in groups of 4-6 mice/cage. Tungstate-free drinking water was administered to the animals during the pre-treatment phase (2 weeks).

Treatment Phase

Sodium tungstate was administered in the drinking water (ad libitum) by means of a 2 mg/ml solution of sodium tungstate dihydrate (marketed by Carlo Erba) in distilled water after the pre-treatment phase (day 0 of treatment) and up to 4 weeks before sacrificing the animals. The daily dose of sodium tungstate ingested by the mice is about 180 mg/kg of body weight.

Mating

After the first three weeks of treatment, the $IRS2^{-/-}$ female mice were housed in cages in pairs together with an $IRS2^{wt}$ male mouse continuously.

The mice were observed daily in search of signs of pregnancy or birth. After 4 weeks, the male mice were exchanged between the cages and kept in said cages for another 4 weeks.

The administration of tungstate was maintained for the 8 weeks in which the male and female mice were housed together. After these 8 weeks, treatment was withdrawn and the male and female mice were housed together for 4 additional weeks.

Sacrifice

After this period lapsed, the female mice were sacrificed and biopsied in search of indications of pregnancy.

C. Results

Results of the Ovulation Study

During the pre-treatment period and during the first 3 weeks of treatment, vaginal smears were performed in 6 randomly chosen female mice on days −8; −5; −2; −1; 7; 8; 14; 15 and 22 to determine the phase of the estrous cycle they were in.

Between 1 and 2 ml of saline solution was introduced into the vagina of the mice with a Pasteur pipette. The vaginal exudate was collected with the same pipette and deposited on a slide. Once air-dried, it was fixed and stained with the Papanicolaou technique.

The Papanicolaou technique comprises staining the vaginal smears fixed on the slide as follows:

10 immersions in 50% v/v alcohol;
immersing in Harris hematoxylin solution for 3 minutes;
rinsing with running water;
10 immersions in acid alcohol (1% hydrochloric acid);
rinsing with running water;
10 immersions in 95% v/v alcohol;
immersing in OG-6 solution for 30 seconds;
10 immersions in 96% v/v alcohol;

immersing in eosin solution for 1 minute;

10 immersions in 96% v/v alcohol;

10 immersions in 86% v/v alcohol; and 10 immersions in xylol.

The preparations were analyzed by trained staff using a code in a single-blind manner to eliminate observer bias.

The samples were identified in the following phases: diestrus, proestrus, estrus, metestrus, anestrus or non-evaluable. The cyclicality of the four phases in periods of 4 to 6 days is an indicator of a normal estrous cycle, whereas the absence of this cyclicality and the persistence in anestrus, diestrus or proestrus phases are indicators of the absence of the estrous cycle.

Of the 10 female mice under study, Table 1 summarizes the phases of the estrous cycle of the vaginal smears performed in 6 of these IRS2$^{-/-}$ female mice.

TABLE 1

| Mouse no. | Time (days) | | | | | | | |
|---|---|---|---|---|---|---|---|---|
| | −8 | −5 | −2 | −1 | 7 | 8 | 14 | 15 | 22 |
| 72 | A | A | P | D | E | E-M | E | E | A |
| 898 | D | D | P | P | E | E | E-M | M | M |
| 926 | D | D | P | P | E-M | E-M | D | E | P |
| 928 | D-P | D | P | P | E | E | E-M | M | A |
| 942 | A | D | P | P | E | E-M | E-M | A | D |
| 972 | D | D | — | P | M | M | — | D | D |

The phases of the estrous cycle are: A: anestrus, D: diestrus, P: proestrus, E: estrus, and M: metestrus.

The phases of the estrous cycle found in the vaginal smears of the IRS2$^{-/-}$ female mice of Table 1 show that during the pre-treatment period all the mice were in the proestrus (P) or diestrus (D) phase, i.e., with the absence of the estrous cycle.

However, after starting the administration of tungstate, it is observed that the IRS2$^{-/-}$ female mice are in the late phases of the estrous cycle, estrus (E) and metestrus (M), which is an indicator of the recovery of the normal estrous cycle.

These results indicate that the administration of a tungsten (VI) salt allows quick recovery (on the seventh day of treatment) of the estrous cycle in infertile, non-diabetic IRS2$^{-/-}$ female mice in 100% of the analyzed mice.

Results of the Implantation and Pregnancy Study

After the mating period of the method in section B lapsed, the female mice were sacrificed and biopsied in search of indications of pregnancy.

Table 2 summarizes the age at the time of treatment, whether or not there was a pregnancy and the number of embryos per female mouse.

TABLE 2

| Mouse no. | Age (months) At the start of | | Pregnancy | Number of implanted embryos or young born |
|---|---|---|---|---|
| | Treatment | Mating | | |
| 72 | 10 | 12 | YES | 1 young |
| 942 | 10 | 12 | YES | 8 young |
| 928 | 10 | 12 | YES | 7 embryos |
| 931 | 10 | 12 | YES | 3 young |
| 898 | 10 | 12 | YES | 7 embryos |
| 900 | 10 | 12 | NO | — |
| 921 | 10 | 12 | YES | 6 embryos |
| 926 | 10 | 12 | YES | 8 young |
| 972 | 8 | 10 | NO | — |
| 973 | 8 | 10 | YES | 7 embryos |

The results of Table 2 show that while the pregnancy rate in untreated IRS2$^{-/-}$ female mice is 9%, the pregnancy rate in IRS2$^{-/-}$ female mice treated with tungstate increases up to 80%.

Furthermore, these results also show that the mean number of young/implanted embryos per female mouse pregnancy is about 5, a number that can be considered as being comparable to the number of young of a female mouse.

Therefore, the results of Tables 1 and 2 demonstrate that a tungsten (VI) salt is effective treatment for recovering ovulation and/or increasing oocyte implantation. Therefore, the administration of a tungsten (VI) salt as defined in the present invention is effective for the treatment of infertility in non-diabetic female mammals.

3. Glycemia and Body Weight Study

A. Animals

6 IRS2$^{-/-}$ female mice of ages comprised between 6 and 8 weeks.

The female mice were housed in normal conditions, i.e., 12-hour light/darkness cycle and controlled moisture and temperature. The animals were voluntarily fed (also named ad libitum) with a standard feed diet.

B. Method

Treatment Phase

After a period of acclimation, sodium tungstate was administered in the drinking water (ad libitum) by means of a 2 mg/ml solution of sodium tungstate dihydrate (marketed by Carlo Erba) in distilled water after the pre-treatment phase (day 0 of treatment) and for 12 days.

C. Results

Body weight was monitored on day 0, 2, 5, 7, 9 and 12 of the treatment period, and after 6 hours of fasting on each of the aforementioned days blood glucose was determined by means of withdrawing blood from the tail vein and with a glucose sensor (Roche AccuTrend Glucose Sensor. Mannheim, Germany).

Table 3 summarizes glycemia levels expressed in mg/dl, and Table 4 summarizes the body weight of the mice under study expressed in grams.

TABLE 3

| glycemia (mg/dl) | R1327 | R1345 | R1347 | R1354 | R1376 | R1381 | Average |
|---|---|---|---|---|---|---|---|
| Day 0 | 146 | 129 | 115 | 126 | 141 | 112 | 128.17 |
| Day 2 | 136 | 128 | 118 | 110 | 105 | 107 | 117.33 |
| Day 5 | 125 | 142 | 114 | 111 | 137 | 105 | 122.33 |
| Day 7 | 140 | 110 | 106 | 89 | 133 | 135 | 118.83 |
| Day 9 | 125 | 153 | 109 | 108 | 131 | 125 | 125.17 |
| Day 12 | 136 | 116 | 111 | 86 | 123 | 141 | 118.83 |

TABLE 4

| Body weight (g) | 1327 | 1345 | 1347 | 1354 | 1376 | 1381 | Average |
|---|---|---|---|---|---|---|---|
| Day 0 | 22.7 | 15.33 | 18.21 | 16.5 | 13.99 | 15.45 | 17.03 |
| Day 2 | 22.9 | 14.84 | 18.98 | 17.01 | 14.18 | 16.04 | 17.33 |
| Day 5 | 22.61 | 14.89 | 18.2 | 16.61 | 13.79 | 15.72 | 16.97 |
| Day 7 | 22.42 | 15.07 | 17.81 | 16.35 | 13.74 | 15.66 | 16.84 |
| Day 9 | 22.85 | 15.56 | 17.9 | 16.89 | 14.5 | 16.39 | 17.35 |
| Day 12 | 23.15 | 15.91 | 18.24 | 17.19 | 14.92 | 16.89 | 17.72 |

The results of Tables 3 and 4 show that during the administration of sodium tungstate no variations are observed in the body weight or in the glycemia in the first 12 days of treatment, the same period in which ovulation in the tested female mice is already successfully re-established starting from day 7 of treatment (cf. Table 1).

Therefore, the results of Tables 1 to 4 demonstrate that a tungsten (VI) salt is effective treatment for recovering ovulation and/or increasing oocyte implantation, regardless of the changes in body weight and changes in carbohydrate metabolism. Therefore, it is demonstrated that the administration of a tungsten (VI) salt as defined in the present invention has a direct effect on the female reproductive system and is therefore effective for the treatment of infertility in non-diabetic female mammals.

The invention claimed is:

1. A method for treating female infertility in a non-diabetic mammal in need thereof, the method comprising administering to said mammal a therapeutically effective amount of a tungsten (VI) salt with a pharmaceutically or veterinarily acceptable cationic group, or a solvate thereof, such that said infertility in said mammal is treated.

2. The method according to claim 1, wherein the mammal is a human.

3. The method according to claim 1, wherein the cationic group is an alkaline or alkaline earth cation.

4. The method according to claim 3, wherein the cationic group is selected from the group consisting of sodium, potassium, magnesium and calcium.

5. The method according to claim 4, wherein the tungsten (VI) salt is the sodium salt of tungsten (VI).

6. The method according to claim 1, wherein the solvate is the dihydrate.

7. The method according to claim 1, where the treatment of female infertility comprises restoring ovulation.

8. The method according to claim 1, wherein the treatment of female infertility comprises increasing zygote implantation in the uterine wall.

9. The method according to claim 1, wherein female infertility occurs with a change in the hypothalamic-pituitary axis.

10. The method according to claim 9, wherein the change in the hypothalamic-pituitary axis is selected from the group consisting of polycystic ovarian syndrome, metabolic syndrome, hyperprolactinemia, endometriosis, eating disorders, obesity, hypothyroidism, multiple sclerosis, rheumatoid arthritis, lupus erythematosus, cirrhosis, celiac disease, chronic renal failure and idiopathic causes.

11. The method according to claim 10, wherein the change in the hypothalamic-pituitary axis is due to idiopathic causes.

12. The method according to claim 10, wherein the eating disorders are selected from anorexia nervosa and bulimia.

13. The method according to claim 1, wherein the tungsten (VI) salt, or a solvate thereof, is part of a pharmaceutical or veterinary composition further comprising pharmaceutically or veterinarily acceptable excipients or carriers.

14. The method according to claim 13, wherein the pharmaceutical or veterinary composition is a composition for oral administration.

15. The method according to claim 14, wherein the composition for oral administration is a liquid composition.

* * * * *